(12) United States Patent
Bujko et al.

(10) Patent No.: US 9,315,552 B2
(45) Date of Patent: Apr. 19, 2016

(54) RECOMBINANT CYTOTOXIN AS WELL AS A METHOD OF PRODUCING IT

(75) Inventors: Anna Bujko, Kalisz (PL); Magdalena Lukasiak, Parzeczew (PL); Jaroslaw Dastych, Lodz (PL); Miroslawa Skupinska, Poznan (PL); Ewelina Rodakowska, Kostrzyn (PL); Leszek Rychlewski, Poznan (PL)

(73) Assignee: BIOINFOBANK SP. Z O. O., Poznan (PL)

( * ) Notice: Subject to any disclaimer, the term of this patent is extended or adjusted under 35 U.S.C. 154(b) by 0 days.

(21) Appl. No.: 13/976,914

(22) PCT Filed: Dec. 29, 2011

(86) PCT No.: PCT/PL2011/050058
§ 371 (c)(1),
(2), (4) Date: Sep. 16, 2013

(87) PCT Pub. No.: WO2012/091590
PCT Pub. Date: Jul. 5, 2012

(65) Prior Publication Data
US 2014/0005362 A1    Jan. 2, 2014

(30) Foreign Application Priority Data
Dec. 31, 2010   (PL) .......................... 393529

(51) Int. Cl.
*C07K 14/21* (2006.01)
*C12N 15/62* (2006.01)
*A61K 38/00* (2006.01)

(52) U.S. Cl.
CPC ............... *C07K 14/21* (2013.01); *C12N 15/62* (2013.01); *A61K 38/00* (2013.01); *C07K 2319/09* (2013.01)

(58) Field of Classification Search
CPC .................. C07K 2319/09; C12N 2810/50
USPC ............................................... 514/1
See application file for complete search history.

(56) References Cited

U.S. PATENT DOCUMENTS 6,045,793 A * 4/2000 Rybak ............ C12Y 301/27005
424/94.6

FOREIGN PATENT DOCUMENTS

| WO | WO 96/26733 | 9/1996 | |
|---|---|---|---|
| WO | WO 2005/120588 A2 | 12/2005 | |
| WO | WO 2006/060044 | * 6/2006 | ............. C07K 14/33 |

OTHER PUBLICATIONS

Hetal Pandya, et al., Genes & Cancer, vol. 1, No. 5, pp. 421-433 (2010).
Allison Lange, et al., JBC, vol. 282, No. 8, pp. 5101-5105 (2007).
Robert J. Kreitman, et al., BioDrugs, vol. 23, No. 1, pp. 1-13 (2009).
Philipp Wolf, et al., International Journal ot Medical Microbiology, vol. 299, pp. 161-176 (2009).
Andrea Bulognesi, et al., British Journal of Haematology, vol. 110, pp. 351-361 (2000).
Yaeta Endo, et al., JBC, vol. 262, No. 12, pp. 5908-5912 (1987).
Andrea Bolognesi, et al., Int. J. Cancer, vol. 68, pp. 349-355 (1996).
Arthur E. Frankel, et al., Cancer, vol. 106, No. 10, pp. 2158-2164 (2006).
Robert J. Kreitman, et al., N Engl J Med, vol. 345, No. 4, pp, 241-247 (2001).
Tadeusz Robak, Current Treatment Options in Oncology, vol. 7, pp. 200-212 (2006).
Daniel Chelsky, et al., MCB, vol. 9, No. 6, pp. 2487-2492 (1989).
Robert J. Kreitman, et al., The AAPS Journal, vol. 8, No. 3, Article 63, E532-E551 (2006).

* cited by examiner

*Primary Examiner* — Karen Cochrane Carlson
(74) *Attorney, Agent, or Firm* — Law Office of Salvatore Arrigo and Scott Lee, LLP (57) ABSTRACT

The subject of the present invention is a method of modifying proteinaceous toxins through the addition of an NLS motif. The resulting cytotoxin facilitates the selective elimination of proliferating cells, particularly tumor cells.

14 Claims, 5 Drawing Sheets

RECOMBINANT CYTOTOXIN AS WELL AS A METHOD OF PRODUCING IT

The subject of the present invention is a method of modifying proteinaceous toxins through the addition of an NLS motif. The resulting cytotoxins facilitate the selective elimination of proliferating cells, particularly tumour cells.

Figure 1:
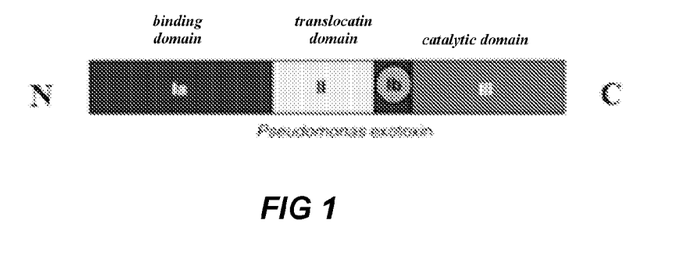
Figure 2:
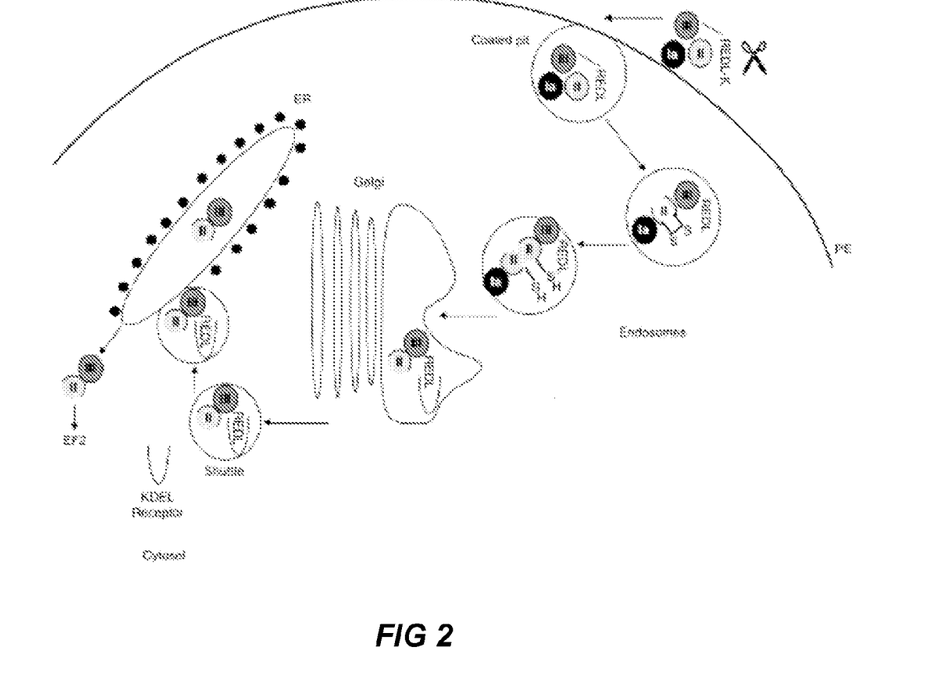
Figure 3:
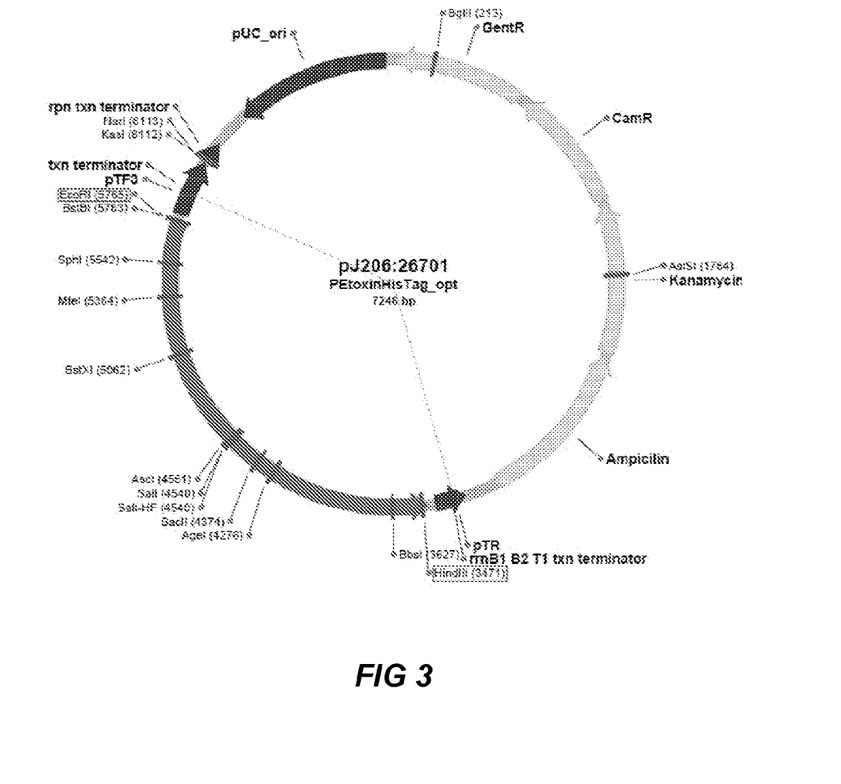
Figure 4:
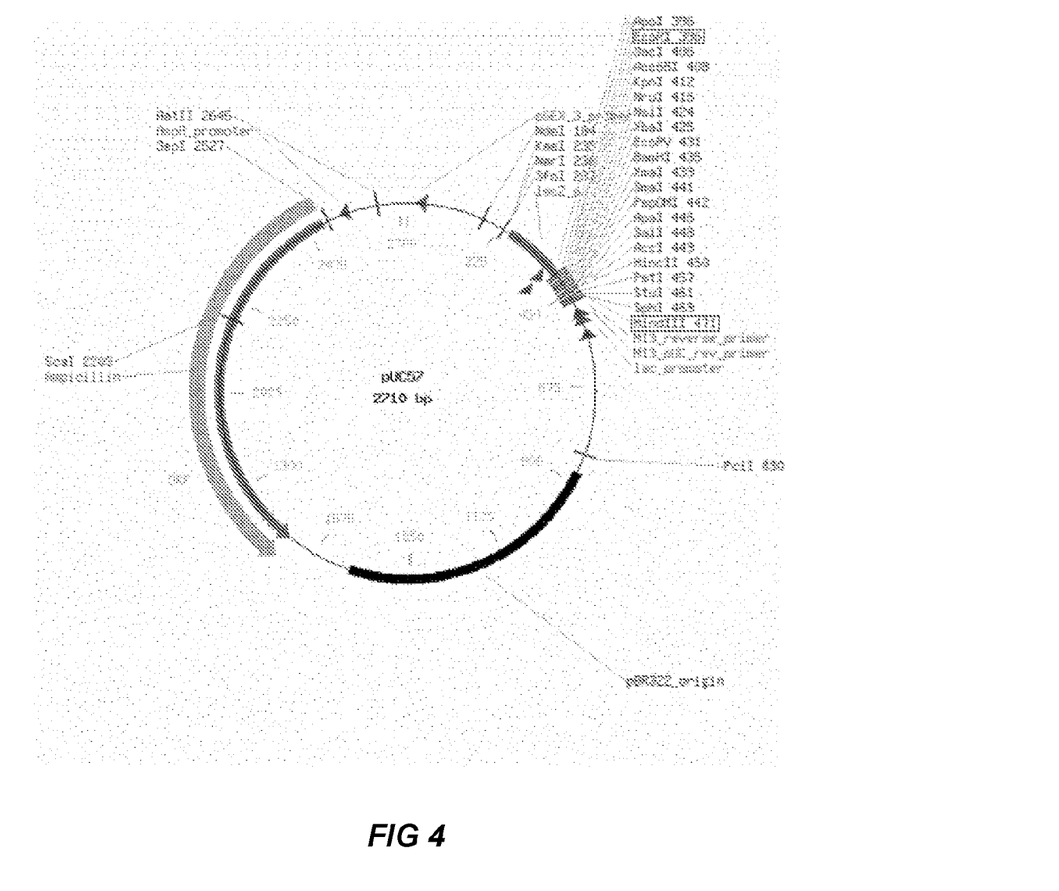
Figure 5:
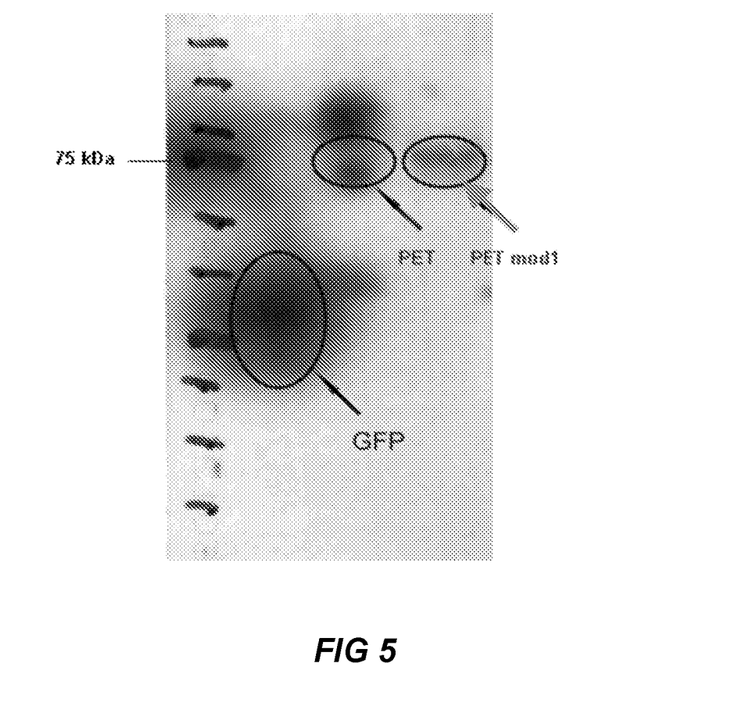
FIG. 5 shows an image of X-ray film with visible signals corresponding to the following proteins: GFP (GFP), native exotoxin (PET) and modified exotoxin (PET modl).
Figure 6:
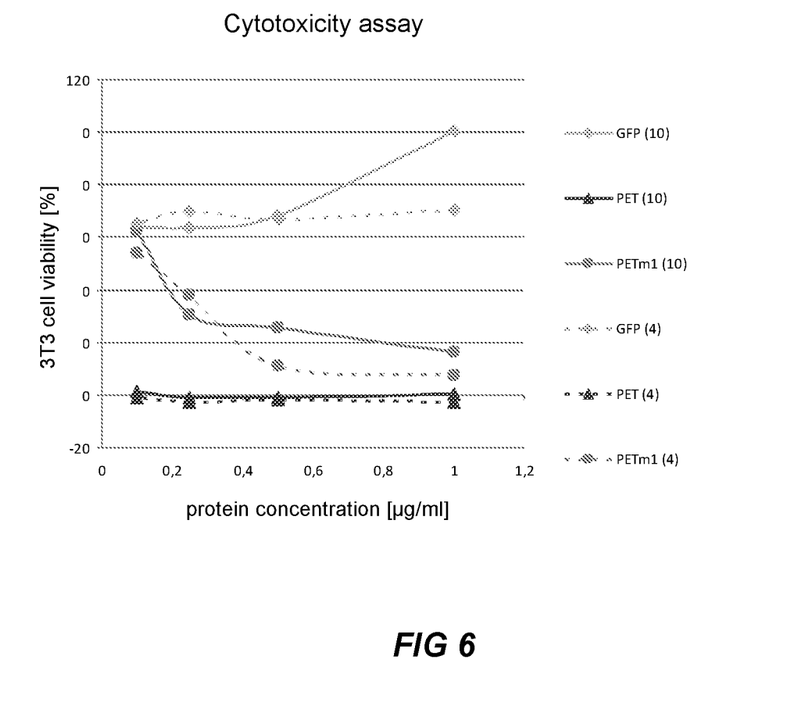
FIG. 6 shows the effect of modified exotoxin (PETm1), native exotoxin (PET) and GFP as controls, on 3T3 fibroblast viability, measurement using the neutral red method after 24h. Culture confluence denoted as: (10)-100% confluence, (4)-40% confluence.

A poison is an organic or inorganic substance which, even at low concentrations, has a deleterious effect on living organisms. Poisons are divided into two basic categories. The first consists of natural poisons, produced mainly by pathogenic bacteria, poisonous fungi and plants, as well as venomous animals. The second group of poisons consists of anthropogenic poisons. Bacterial toxins (venoms) are various chemical compounds produced by bacteria which poison a higher organism. They act specifically on various systems (i.e. on the gastrointestinal tract) or cells of an organism (i.e. neurotoxins). These are differentiated into exotoxins and endotoxins. Exotoxins, secreted outside of the live cell are strong venoms and induce specific disease symptoms. They have a proteinaceous structure (metabolic product) and thus are sensitive to high temperatures (>60° C.) as well as being degraded by digestive enzymes (with the exception of botulinum toxin and *Staphylococcus* enterotoxins). They have strong antygenic properties, and anatoxins made therefrom are used to immunise humans and animals. They are made mainly by Gram-positive bacteria. These are some of the strongest toxic substances known. Endotoxins are released only following the degradation of the bacterial cell. They are weak venoms, and the symptoms they induce are not specific. Chemically, these are glycolipopolypeptide complexes (lipopolysaccharide) which most often occur in Gram-negative bacteria in one of the three cell-wall layers. They are poorly antygenic. They are not degraded by digestive enzymes but are thermostable. Exotoxins secreted by bacteria (but also by plants, fungi and some animals) exhibit cytotoxic properties against a host cells, usually due to the enzymatic inhibition of protein synthesis. The essential condition toxin activity is their binding of surface receptors on the target cell and their internalisation through endocytsis, and then translocation from the endoplasmatic reticulum into the cytosol. Bacterial exotoxins are currently produced using genetic engineering methods or chemically conjugated with ligands and antibodies so as to bind to specific cell types. This facilitates the selective destruction of disease-altered cell lines. The use of bacterial exotoxins specific for tumour cells is one of the targeted therapeutic strategies against cancer. Exotoxins secreted naturally by the disease-causing bacteria *Pseudomonas aeruginosa* and *Diphtheriae typhimurium* are compounds of very high cytotoxicity, sometimes many times higher than of classic antitumour drugs. In many cases a single toxin molecule is capable of killing a cell, which makes them some of the most lethal compounds. An exotoxin frequently used to construct fusion proteins with antitumour activity is exotoxin PE from *Pseudomonas aeruginosa* (*Pseudomonas* exotoxin, PE) [1]. A molecule of native PE toxin consists of a catalytic domain connected with a domain that binds a receptor through a central translocation domain, which facilitates the transfer of the C-terminal catalytic domain into the cytosol (FIG. 1). So far, the role of the Ib domain of PE remains unknown, but it is known that it contains a disulphide bridge necessary for molecule maturation. FIG. 2 shows the mechanism of PE intoxication. Due to the interaction with the host cell, PE binds to the α2 macroglobulins. Prior to entering the cell, the toxin is cleaved proteolytically. A caroxypeptidase cuts off the terminal lysine which exposes the REDL motif. Next, the exotoxins are internalised through endocytosis dependent on the receptor. After entering endocytotic vesicles, the toxin is cleaved proteolytically by furin inside the translocation domain, and the disulphide bridges hold the formed fragments until they are reduced. The PE migration pathway in the cell is through the Golgi apparatus and encompasses retention in the endoplasmatic reticulum due to the REDL signal at the C-terminus of the protein. Then, the freed catalytic domain is translocated through the reticulum wall into the cytosol. There, the active protein catalyses ADP-ribosylation of His at position 699 of the translation factor eEF2 and thereby inhibits protein synthesis, thereby quickly leading to cell death [1]. The use of PE in targeted therapy entails the replacement of the receptor-binding domain with an antibody or a portion thereof, a cytokine or growth factor (hence the name immunotoxins). The most frequently used form of PE is a fractional exotoxin of 38 kDa composed of amino-acids 253-364 and 381-613. Chimeric immunotoxins based on PE molecules are most often directed against receptors IL2 and IL6 as well as growth factor TGFα (Tab. 1) [2]. The table below lists information regarding the use of propharmaceuticals containing immunotoxins in the treatment of tumours (clinical trials).

TABLE 1

Immunotoxins based on PE in clinical trials, 2009 data [2]

| Immunotoxin | Construction | Target antigen | Tumors | References |
| --- | --- | --- | --- | --- |
| CD19-ETA' | scFv fused to PE38KDEL | CD19 | Lymphoma, leukemia | Schwemmlein et al. (2007) |
| Anti-Tac(Fv)-PE38KDEL [LMB2] | scFv fused to PE38KDEL | CD25 | CD25 positive tumor cells | Kreitman et al. (1994) |
| Anti-Tac(Fv)-PE40KDEL | scFv fused to PE40KDEL | CD25 | Chronic lymphocytic leukemia | Kreitman et al. (1992) |
| RTF5(scFv)-ETA' | scFv fused to PE40 | CD25 | Lymphoma | Barth et al. (1998) |
| RFB(dsFv)-PE38 [B1.22] | dsFv fused to PE38 | CD22 | B-cell leukemia | Kreitman et al. (2000a) |
| G28-5 sFv-PE40 | scFv fused to PE40 | CD40 | Burkilt's lymphoma | Francisco et al. (1997) |
| Ki4(scFv)-ETA' | scFv fused to PE40 | CD30 | Hodkin's lymphoma | Klimka et al. (1999) |
| CD7-ETA | scFv fused to PE40 | CD7 | T-lineage acute lymphoblastic leukemia | Peipp et al. (2002) |
| OVB3-PE | mAb linked via disulfide bond to PE | Ovary | Ovarian | Willingham et al. (1987) |
| B3-Lys-PE38 [LMB-1] | mAb chemically linked to PE38 | LeY | Various | Pastan (1997) |
| B1(dsFv)-PE38 | dsFv fused to PE38 | LeY | LeY positive tumor cells | Benhar et al. (1995) |
| B3(dsFv)-PE38 | dsFv fused to PE38 | LeY | LeY positive tumor cells | Benhar et al. (1995) |
| BR96sFv-PE40 [SGN-10] | scFv fused to PE40 | LeY | LeY positive tumor cells | Friedman et al. (1993) |
| IL4(38-37)PE38KDEL [NBI-3001] | IL4 fused to PE38KDEL | IL4-R | Breast, SCCHN, pancreas, medulloblastoma | Leland et al. (2000); Kawakami et al. (2000, 2002); Strome et al. (2002); Joshi et al. (2002) |

TABLE 1-continued

Immunotoxins based on PE in clinical trials, 2009 data [2]

| Immunotoxin | Construction | Target antigen | Tumors | References |
|---|---|---|---|---|
| IL13-PE38QQR | IL13 fused to PE38QQR | IL13-R | Head and neck | Kawukumi et al. (2001) |
| scFv(FRP5)-ETA | scFv fused to PE40 | erbB2 | Ovarian, prostate | Wels et al., (1992); Schmidt et al. (2001); Wang et al. (2001) |
| AR209 [e23(Fv)PE38KDEL] | scFv fused to PE38KDEL | erbB-2 | Lung, prostate | Skrepnik et al. (1996, 1999); |
| Erb-38 | dsFv fused to PE38 | erbB2 | Epidermoid carcinoma, breast | Reiter and Pastan (1996) |
| MR1(Fv)-PE38 | scFv fused to PE38 | EGFRvIII | Glioblastoma | Beers et al. (2000) |
| TP38 | TGF-α fused to PE38 | EGFR | Glioma | Sampson et al. (2003) |
| TP40 | TGF-α fused to PE40 | EGFR | Glioma, prostate, epidermoid | Sarosdy et al., (1993); Pai et al. (1991a); Kunwar et al. (1993) |
| 425.3PE | mAb chemically linked to PE | EGFR | Breast | Andersson et al. (2004) |
| A5-PE40 | scFv fused to PE40 | PSMA | Prostate | Wolf et al. (2006, 2008) |
| SS1(dsFv)PE38 [SSIP] | dsFv fused to PE38 | Mesothelin | Ovarian, cervical | Hussan et al. (2002) |
| scFv(MUC1)-ETA | scFv fused to PE40 | MUC1 | Breast | Singh et al. (2007) |
| 9.2.27-PE | mAb chemically linked to PE | HMW-MAA | Gliomblastoma | Hjortland et al. (2004) |
| TP-3(scFv)-PE38 | scFv fused to PE38 | Osteosarcoma antigen | Osteosarcoma | Onda et al. (2001) |
| TP-3(dsFv)-PE38 | dsFv fused to PE38 | Osteosarcoma antigen | Osteosarcoma | Onda et al. (2001) |
| 8H9(dsFv)-PE38 | dsFv fused to PE38 | Cell surface glycoprotein | Breast, osteosarcoma, neuroblastoma | Onda et al. (2004) |
| 4D6MOCB-ETA | scFv fused to PE40KDEL | Ep-CAM | Lung, colon, SCC | Di Panlo et al. (2003) |
| HB21(Fv)-PE40 | scFv fused to PE40 | TfR | Colon | Shinohara et al. (2000) |

Denileukin diftitox (ONTAK) is at present the only available therapeutic which is an immunotoxin. Registered in 1999, it is used in the therapy of CTCL, Cutaneous T-Celi Lymphoma. The FDA report of 16.10.2008 gives it a full marketing permits.

The distribution of cell surface antigens used in targeted therapy is very often not limited to tumour cells, but is only characterised by increased frequency in comparison to normal cells. This often causes side effects during the use of the drugs in the form of the destruction of healthy cells, even in tissues and organs with different functions. For example, in the therapy of breast cancer targeted against HER2 receptors, one observes the non-specific ingress of immunotoxins into hepatocytes or macrophages, which induces liver damage, and the release of cytokines by the macrophages causes subsequent non-specific changes. Newest generation immunotoxins are characterised by a higher specificity, stemming from the fact that their binding-activity requires not one, but two or more factors specific to tumour cells.

The goal of the present invention is to deliver a compound, whose activity will be dependent on the phase of the cell cycle and will be preferably apparent in intensively proliferating cells, particularly tumour cells. It is desirable that the sought substance, in addition to binding specifically defined epitopes, is subject to specific activation in cancerous cells. This type of substance should be fit for use in the production of novel pharmaceutical compositions characterised by increased therapeutic efficiency w the treatment of tumours as well as a lower number of undesirable side effects.

Unexpectedly, the above stated goal has been achieved in the present invention.

The subject of the present invention is a method of modifying a protein toxin through the addition of an NLS motif, which unexpectedly decreases the toxicity of the resulting toxin towards non-proliferating cells. In the example embodiment of the present invention we design a fusion protein containing the amino-acid sequence encompassing the sequence of bacterial exotoxin as well as the sequence of a human NLS motif.

For the purposes of this description, "protein toxins" should be understood as natural polypeptides with toxic properties, such as:

neurotoxins, which hinder neurotransmission,
enterotoxins, which damage the gastrointestinal mucosa,
cytotoxins, which destroy cells Protein toxins may be of various origins. Known are the following toxins:

animal i.e.: Cubozoa venom contains protein toxins with neurotoxic and cardiotoxic properties, which also cause tissue necrosis; Taipoxin (*Oxyuranus scutellatus*), inhibits acetylcholine release from terminal neurons and some cholinergic neurons of the autonomous nervous system; o-latrotoxin (*Latrodectus*) binds with membrane neurexins and causes the sudden depletion of synaptic vesicles;

fungal i.e.: α-amanitin (deathcap mushroom), binds with RNA polymerase II, at higher concentrations also with RNA polymerase III, preventing RNA elongation during synthesis; α-sarcin (*Aspergillus giganteus*) inhibits protein synthesis by hydrolyzing phosphodiester bonds in 28S RNA in the large ribosomal subunit;

plant i.e.: Holotoxins (also called class II ribosome-inactivating proteins) i.e.: ricin (castor oil plant), abrin (rosary pea), lectin (mistletoe), modecin (*Adenia digitata*); Hemitoxins (also called class I ribosome-inactivating proteins) i.e.: PAP (pokeweed antiviral protein), saporin (*Saponaria officinalis*), bouganin (*Bougainvillea spectabilis*) and gelonin (*Gelonium Multiflorum*) [3]; (Holotoxins are composed of a binding domain and a catalytic domain whereas hemitoxins contain only a catalytic domain. Plant toxins inhibit the binding of the elongation factors EF-1 and EF-2 with the ribosomal 60S subunit by removing the A residue in position 4324 of 28SRNA. Ricin also removes the neighbouring G residue at position 4323 [4]. The result of such toxin activity is cell death via apoptosis. Only the enzymatic domain is translocated into the cytoplasm, and thus the binding domain of holotoxins is cleaved off through the reduction of the disulphide bond [5-7].);

bacterial i.e.: Neurotoxins: botulin (*Clostridium botulinum*) (the activity *botulinum* toxin is based on permanent affixation to the neuromotor plate and disruption of muscle contraction. This is done by the fragmentation of the SNAP-25 protein essential to acetylcholine secretion from the presynaptic terminus), tetanus toxin, tetanospasmin (*Clostridium tetani*) (tetanospasmin binds to peripheral motor neurons, enters the axon and from there transfers to neurons of the brain stem and spinal chord. It then migrates through the synapse to the presynaptic terminus where it blocks the release of neurotransmitters (glycine and GABA); Enterotoxins: streptolysine O (*Streptococcus pyogenes*), listeriolysine O (*Listeria monocytogenes*), alpha-toxin (*Staphylococcus aureus*) (these toxins are capable of integrating into the cell membrane in which they form channels. In this way the porous membrane can no longer function, and ions begin to egress the cell whereas water begins to flow inside and the cell may swell and lyse.); Cytotoxins: collagenases, hyaluronidases or phospholipases are enzymes which respectively degrade collagen (facilitating deep penetration of tissue) and membrane phospholipids; Shiga toxin, Stx (*Shigella dysenteriae*) this protein is composed of 6 subunits: 5 B subunits, responsible for binding the toxin to its receptor—globotriaosylceramide (Gb3) of a eukaryotic cell and an A subunit, which is proteolysed following endocytosis to peptides A1 and A2. StxA2 is an enzyme which cleaves an adenine off 28S ribosomal RNA. This inhibits tprotein synthesis in a cell and its death; cholera toxin (*Vibrio cholerae*) catalyses the binding of ADP-ribose to a G-protein subunit which lose its GTPase activity. It fails to dissociate from adenylate cyclase, of which it is an activator. Surplus synthesis of cyclic AMP causes an increased concentration of electrolytes in the intestinal lumen (storage of chlorides and inhibited potassium absorption), which causes constant water flow into the intestines; dyphtherotoxin (*Corynebacterium diphtheriae*), a transferase which transfers ADP-ribose from NAD+ to eEF-2 (ADP-ribosylation) and in this way inhibits the translocation and thus the elongation of a polypeptide chain; exotoxin A (*Pseudomonas*).

For the purposes of this description, "immunotoxins" should be understood as complexes of antibodies or their fragments with toxins, chemically bound. The antibody is directed against structures on the tumour cell surface. Most often, recombinant immunotoxins produced by *E. coli* are used, such as:

human interleukin-2 (IL-2) combined with dophthitoxin (denileukin diftitox)—reacts with the IL-2 receptor. This drug is registered for the treatment of dermal T-cell lymphomas. It has also been tested in CLL patients resistant to other antileukaemia drugs [8]. Denileukin diftitox is administered at a rate of 18 μg/kg/day in a 60 minute infusion over five days at 21 day intervals. Up to 8 combined cycles have been used. In 12 patients, reduced leukaemic cells have been observed in the blood of over 80% of the patients, and in 6 a decrease in lymph node volume. 6 of 22 patients who received at least 2 cycles fulfilled the criteria for full or partial remission.

BL22—a recombinant immunotoxins containing an IgG immunoglobulin fragment, which recognizes antigen CD22, conjugated with the exotoxin of Pseudomonas [9]. The antibody is highly active in the case of hairy cell leukaemia [10.11]. A high efficacy was also observed against CLL but not against CR [11,12]. Currently, a BL22 mutant termed HA22 is undergoing clinical trials [9].

For the purposes of this description the human "NLS" motif (nuclear localization signal or sequence) should be understood as an amino-acid sequence motif warranting intracellular transport of a protein into the nucleus. It comprises a sequence of positively charged amino-acids, lysines and arginines (so-called single NLS), meeting the consensus K-K/R-X-KR with the sequence: KKKRKR [13].

An example use of the present invention is exotoxin A of *Pseudomonas aeruginosa* modified such that in the amino-acid sequence it contains an additional NLS motif: KKKRKR added at position -633, behind proline -632 from the amino end (as shown in sequence 1) in relation to the native protein.

The next subject of the present invention are nucleotide sequences of DNA, cDNA and mRNA encoding exotoxin A of *Pseudomonas aeruginsa* modified such that at position 1933 in relation to the native sequence the additionally contain a motif encoding NLS, taking into account the degeneration of genetic code, meaning that all DNA encodes the protein with the amino-acid sequence according to the present invention as it has been defined above. Particular embodiment of the nucleotide sequence according to the present invention is sequence 2.

The next subject of the present invention are modified proteins, derivatives of exotoxins containing the protein fragment described above, with the modification described above, as well as the DNA sequences encoding them.

The next subject of the present invention are recombinant expression vectors as well as expression cassettes containing said DNA sequences.

The next subject of the present invention is the production of said proteins through overexpression in cells and in extracellular systems.

The next subject of the present invention is the use of said proteins to treat eukaryotic cells.

The next subject of the present invention the use of said proteins in the production of pharmaceutical compositions.

The description of the present invention is illustrated by the attached figures. FIG. 3 represents a schematic representation of the structure of the exoPE toxin [14]. FIG. 4 represents the mechanism of PE intoxication.

To better understand the present invention defined above, the present description also contains an example embodiment of the present invention. This example, however, should not be treated as limiting the scope encompassed by the present invention. The example embodiments are illustrated by the attached figures, wherein FIG. 3 shows the map of the vector pJ206, wherein the frame encloses the restriction sites EcoRI and HindIII. FIG. 4 shows the map of the vector pUC57, where the frame encloses the restriction sites for EcoRI and HindIII. FIG. 5 in turn shows an X-Ray film with visible signals corresponding to GFP (GFP), native exotoxin (PET) as well as modified exotoxin (PET mod1). FIG. 6. shows the effect of the selected chimeric toxins on live human fibroblasts, 3T3, neutral red method after 24 h, where: GFP—translation from the vector with GFP (translation control), PETm1—translation from the vector with the modified toxin whereas PET is the native toxin.

BRIEF DESCRIPTION OF THE DRAWINGS

FIG. 1 shows a schematic of the structure of PE exotoxin of Pseudomonas aeruinosa. According to: Kreitman (2009), modified.

FIG. 2 shows a schematic of PE intoxication. Source: Kreitman (2009).

FIG. 3 shows a map of vector pJ206:26701. Red frames delineate restriction sites for EcoRl and Hindlll.

FIG. 4 shows a map of vector UC57. Red frames delineate restriction sites for EcoRI and HindIII.

EXAMPLE 1

The sequence encoding the modified exotoxin was designed with the further addition of elements necessary to obtain (via in vitro synthesis) proteins containing a tag in the form of 6 histidine residues. The nucleotide sequence of the entire expression cassette is shown as sequence No. 3 whereas the protein it encodes has the amino-acid sequence termed sequence 4 (in the sequence list).

The expression cassette containing: a promoter for the T7 polymerase, a ribosome binding site, a start codon, a linker with the His-tag as well as a sequence encoding the modified exotoxin; was obtained through chemical synthesis performed by the GenScript company. This cassette was then cloned by the producer into the vector pJ206 between the restriction sites EcoRI and HindIII (FIG. 1). From such a vector we digested out the entire expression cassette and transcloned it into the plasmid pUC57 (FIG. 2) using the EcoRI and Hind III restrictases. In the same way we synthesized and prepared the vectors used to express proteins that were the controls in the experiment: unmodified (native) exotoxin A of *Pseudomonas aeruginsa* as well as GFP.

The vector containing the insert, the expression cassette for the modified exotoxin as well as vectors for the expression of the native exotoxin and GFP were used for in vitro transcription and translation using the commercial "RTS 100 *E. coli* HY Kit containing *E. coli* lysate (5Prime)". Proteins synthesized in this fashion were purified on Ni-NTA-agarose (Qiagen) and dialysed against PBS, and then concentrated using Amicon centrifuge filters. The concentration of the resulting proteins in subsequent purification steps was estimated using the BCA method (Tab. 2).

TABLE 2

Concentrations of proteins obtained via in vitro transcription/translation, estimated using the BCA method.

| | protein concentration [μg/ml] | |
|---|---|---|
| | preparation cleaned on Ni-NTA-agarose | preparation following concentration on Amicon filters |
| GFP | 75 | 227 |
| PET | <10 | 39 |
| PET_mod1 | 22 | 64 |

The molecular mass of the resulting proteins was evaluated using electrophoresis on Agilent microchips. The results are shown below (Tab. 3) and reflect the predicted mass of the resulting polypeptides.

TABLE 3

Molecular mass of the proteins obtained through in vitro transcription/translation, evaluated using the Agilent microchip.

| | mass [kDa] |
|---|---|
| GFP | 30 |
| PET | 74 |
| PET_mod1 | 76 |

To confirm that the resulting fusion protein of the desired mass was obtained, we performed Western blot analysis. Detection was performed using an antibody against the His-tag, conjugated with HRP (horseradish peroxidase). As is shown in FIG. 3, all resulting proteins bound the anti-His-tag antibody. The resulting signals corresponded to a mass of about 30 kDa (GFP) and 75 kDa (native and modified toxins).

We then tested the effect of the modified toxins on the growth of NIH/3T3 mouse fibroblasts and its selective cytotoxic effect on intensively dividing cells. FIG. 4 shows a compilation of survivability results of the treated cells. In the case of modified exotoxin, we observed differences dependent on the stage of development of the culture (confluence of 100% and 40%). Intensively dividing cells (initial confluence 40%) were more sensitive to the modified exotoxin than 100% confluent cells, and the difference was about 11%.

REFERENCES

1. Kreitman R J. Recombinant immunotoxins containing truncated bacterial toxins for the treatment of hematologic malignancies. *BioDrugs.,* 2009, 23(1):1-13.
2. Wolf P, Elsässer-Beile U. *Pseudomonas* exotoxin A: from virulence factor to anti-cancer agent. Int J Med Microbiol. 2009, 299, 161-76.
3. Bolognesi A, Polito L, Tazzari P L, et al. In vitro anti-tumour activity of anti-CD80 and anti-CD86 immunotoxins containing type 1 ribosome inactivating proteins. *Br J Haematol.* 2000; 110: 351- 361.
4. Endo Y, Mitsui K, Motizuki M, Tsurugi K. The mechanism of action of ricin and related toxic lectins on eukaryotic ribosomes. *J Biol Chem.* 1987; 262: 5908-5912.
5. Bolognesi A, Tazzari P L, Olivieri F, Polito L, Falini B, Stirpe F. Induction of apoptosis by ribosome-inactivating proteins and related immunotoxins. *Int J Cancer.* 1996; 68: 349-355.
6. Hughes J N, Lindsay C D, Griffiths G D. Morphology of ricin and abrin exposed endothelial cells is consistent with apoptotic cell death. *Hum Exp Toxicol.* 1996; 15: 443-451.
7. Bergamaschi G, Perfetti V, Tonon L, et al. Saporin, a ribosome inactivating protein used to prepare immunotoxins, induces cell death via apoptosis. *Br J Haematol.* 1996; 93: 789-794.
8. Frankel A E, Surendranathan A, Black J H, White A, Ganjoo, Cripe L D. Phase II clinical studies of denileukin diffitox fusion protein in patients with previously treated chronic lymphocytic leukemia. Cancer. 2006; 106: 2158-2164.
9. Robak T. Novel monoclonal antibodies for the treatment of chronic lymphocytic leukemia. Curr Cancer Drug Targets. 2008; 8: 156-171.
10. Kreitman R J, Wilson W H, Bergeron K, et al. Efficacy of the anti CD22 recombinant immunotoxins BL22 in chemotherapy resistant hairy cell leukemia. N Engl J Med. 2001; 345: 241-247.

11. Robak T. New agents in chronic lymphocytic leukemia. Curr Treat Options Oncol. 2006; 7: 200-212.
12. Kreitman R J, Squires D R, Stetler-Stevenson M, et al. Phase I trial of recombinant immunotoxins RFB4 (dsFv)-PE38 (BL22) in patients with B-cell malignancies. J Clin Oncol. 2005; 23: 6719-6729.
13. Chelsky D, Ralph R, Jonak G. Sequence requirements for synthetic peptide-mediated translocation to the nucleus. Mol Cell Biol. 1989 Jun; 9(6):2487-92.
14. Kreitman R. J. Immunotoxins for targeted cancer therapy. AAPS J. 2006 Aug 18; 8(3):E532-51.

The invention claimed is:

1. A method of producing a recombinant cytotoxic exotoxin, the method comprising adding a human nuclear localization signal (NLS) motif amino acid sequence to the amino-acid sequence of a starting protein cytotoxic exotoxin to provide a recombinant cytotoxic exotoxin comprising an amino acid sequence consisting of the amino acid sequence of the starting protein cytotoxic exotoxin and the added NLS, wherein the resulting recombinant cytotoxic exotoxin has a decreased overall cytotoxicity in comparison to the cytotoxicity of the starting protein cytotoxic exotoxin.

2. A recombinant cytotoxic exotoxin protein comprising an amino-acid sequence consisting of the amino acid sequence of a starting protein cytotoxic exotoxin and the amino acid sequence of an added human NLS motif, wherein the recombinant cytotoxic exotoxin protein has a decreased overall cytotoxicity in comparison to the cytotoxicity of the starting protein cytotoxic exotoxin.

3. The recombinant cytotoxic exotoxin protein according to claim 2, wherein the protein cytotoxic exotoxin is a bacterial exotoxin.

4. The recombinant cytotoxic exotoxin protein according to claim 2, wherein the starting protein cytotoxic exotoxin is exotoxin A of Pseudomonas aeruginosa.

5. The recombinant cytotoxic exotoxin protein according to claim 2, wherein the recombinant cytotoxic exotoxin protein is an immunotoxin.

6. The recombinant cytotoxic exotoxin protein according to claim 2, wherein the NLS motif comprises the amino-acid sequence KKKRKR (positions 633 to 638 of SEQ ID NO: 1).

7. The recombinant cytotoxic exotoxin protein according to claim 4, wherein the NLS motif comprises the amino-acid sequence KKKRKR (positions 633 to 638 of SEQ ID NO: 1).

8. The recombinant cytotoxic exotoxin protein according to claim 2, comprising the amino-acid sequence shown as SEQ ID NO: 1 or SEQ ID NO: 4.

9. A polynucleotide encoding the recombinant cytotoxic exotoxin protein according to claim 2.

10. A polynucleotide encoding the recombinant cytotoxic exotoxin protein according to claim 8.

11. A polynucleotide according to claim 10, comprising the nucleotide sequence shown as SEQ ID NO: 2 or SEQ ID NO: 3.

12. A biologically active vector, comprising a polynucleotide according to claim 9.

13. A biologically active vector, comprising a polynucleotide according to claim 10.

14. A biologically active vector, comprising a polynucleotide according to claim 11.

* * * * *

SEQUENCE LISTING

```
<160> NUMBER OF SEQ ID NOS: 4

<210> SEQ ID NO 1
<211> LENGTH: 643
<212> TYPE: PRT
<213> ORGANISM: artificial sequence
<220> FEATURE:
<223> OTHER INFORMATION: fusion protein

<400> SEQUENCE: 1

Met His Leu Thr Pro His Trp Ile Pro Leu Val Ala Ser Leu Gly Leu
1               5                   10                  15

Leu Ala Gly Gly Ser Phe Ala Ser Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
            115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Ala Gln Pro Arg Arg
            195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
            275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320
```

```
Ala Leu Tyr Leu Ala Ala Arg Leu Ser Trp Asn Gln Val Asp Gln Val
            325                 330                 335
Ile Arg Asn Ala Leu Ala Ser Pro Gly Ser Gly Asp Leu Gly Glu
            340                 345                 350
Ala Ile Arg Glu Gln Pro Glu Gln Ala Arg Leu Ala Leu Thr Leu Ala
            355                 360                 365
Ala Ala Glu Ser Glu Arg Phe Val Arg Gln Gly Thr Gly Asn Asp Glu
            370                 375                 380
Ala Gly Ala Ala Ser Ala Asp Val Val Ser Leu Thr Cys Pro Val Ala
385                 390                 395                 400
Ala Gly Glu Cys Ala Gly Pro Ala Asp Ser Gly Asp Ala Leu Leu Glu
            405                 410                 415
Arg Asn Tyr Pro Thr Gly Ala Glu Phe Leu Gly Asp Gly Gly Asp Ile
            420                 425                 430
Ser Phe Ser Thr Arg Gly Thr Gln Asn Trp Thr Val Glu Arg Leu Leu
            435                 440                 445
Gln Ala His Arg Gln Leu Glu Glu Arg Gly Tyr Val Phe Val Gly Tyr
            450                 455                 460
His Gly Thr Phe Leu Glu Ala Ala Gln Ser Ile Val Phe Gly Gly Val
465                 470                 475                 480
Arg Ala Arg Ser Gln Asp Leu Asp Ala Ile Trp Arg Gly Phe Tyr Ile
            485                 490                 495
Ala Gly Asp Pro Ala Leu Ala Tyr Gly Tyr Ala Gln Asp Gln Glu Pro
            500                 505                 510
Asp Ala Arg Gly Arg Ile Arg Asn Gly Ala Leu Leu Arg Val Tyr Val
            515                 520                 525
Pro Arg Ser Ser Leu Pro Gly Phe Tyr Arg Thr Gly Leu Thr Leu Ala
            530                 535                 540
Ala Pro Glu Ala Ala Gly Glu Val Arg Leu Ile Gly His Pro Leu
545                 550                 555                 560
Pro Leu Arg Leu Asp Ala Ile Thr Gly Pro Glu Glu Gly Gly Arg
            565                 570                 575
Leu Glu Thr Ile Leu Gly Trp Pro Leu Ala Glu Arg Thr Val Val Ile
            580                 585                 590
Pro Ser Ala Ile Pro Thr Asp Pro Arg Asn Val Gly Gly Asp Leu Asp
            595                 600                 605
Pro Ser Ser Ile Pro Asp Lys Glu Gln Ala Ile Ser Ala Leu Pro Asp
            610                 615                 620
Tyr Ala Ser Gln Pro Gly Lys Pro Lys Lys Arg Lys Arg Arg Glu
625                 630                 635                 640
Asp Leu Lys

<210> SEQ ID NO 2
<211> LENGTH: 1968
<212> TYPE: DNA
<213> ORGANISM: artificial sequence
<220> FEATURE:
<223> OTHER INFORMATION: sequence encoding fusion protein

<400> SEQUENCE: 2
atgagcggtt ctcatcacca tcaccaccat agcagcggta ttgaaggtcg catgcacctg    60
accccacact ggattccact ggtcgcgagc ctgggcctgc tggcgggtgg cagctttgcg   120
agcgctgcag aagaggcctt cgacctgtgg aatgagtgtg cgaaagcatg tgttctggac   180
```

```
ttgaaggatg cgttcgcag cagccgcatg agcgtcgatc cggcaattgc ggataccaac        240
ggtcaaggtg ttctgcatta tagcatggtt ctggaaggtg caatgacgc gctgaagttg        300
gcgatcgaca atgcgctgag cattacctct gatggcctga cgattcgcct ggagggtggt      360
gttgagccga acaaaccagt ccgctacagc tacacccgtc aagcgcgcgg tagctggagc      420
ctgaactggc tggttccgat cggtcacgaa aaacctagca acatcaaggt tttcattcat      480
gagctgaacg ctggcaatca actgtcgcac atgagcccga tttataccat tgaaatgggt      540
gatgagctgc tggccaagct ggcacgtgat gcaacgtttt cgtccgtgc ccacgaatct       600
aatgagatgc aacctacgct ggctatcagc cacgcgggcg tgagcgttgt gatggcccaa      660
gcgcaaccgc gtcgtgagaa cgttggagc gaatgggcca cggcaaggt tctgtgtttg        720
ctggatccgc tggacggtgt gtacaattat ctggcgcagc agcgttgcaa cctggatgac      780
acctgggaag gtaagattta tcgtgtgctg gccggtaatc ctgcaaaaca tgacctggac     840
attaaaccga ccgtcatctc ccaccgcctg cacttcccgg agggcggtag cttggcagca      900
ctgaccgcac accaggcgtg ccatctgccg ctggaaacct tcacccgtca ccgtcagccg      960
cgtggttggg aacagctgga gcaatgcggt tatccagtgc aacgtctggt cgcactgtac     1020
ctggcggcgc gcctgtcctg gaatcaggtc gaccaggtga tccgtaacgc attggcaagc     1080
ccgggcagcg gtggtgatct gggcgaggcc atccgtgagc aaccggagca agcacgtctg     1140
gcactgaccc tggccgccgc cgaaagcgaa cgcttcgttc gtcaaggtac tggtaatgac     1200
gaggcgggtg cggcctccgc ggatgtcgtg agcctgacgt gcccggttgc tgcgggtgag     1260
tgcgcgggtc cggctgacag cggcgatgct ctgctggagc gtaattatcc gaccggtgcc     1320
gaatttctgg cgacggtgg cgatatcagc ttcagcacgc gcggtactca gaactggacc     1380
gttgaacgcc tgctgcaggc gcatcgtcag ctggaggaac gtggctatgt ttttcgtcggt    1440
taccacggta cttttcctgga agctgcacaa agcattgttt ttggcggtgt ccgtgcacgc    1500
agccaggacc tggatgcgat ctggcgtggt ttctacatcg ccggtgaccc ggcgctggcg     1560
tacggctatg ctcaagatca agaaccggat gcgcgtggtc gtattcgcaa tggtgcattg     1620
ctgcgtgtgt atgtcccacg tagcagcttg ccgggttctct accgtacggg tttgacgctg    1680
gcagcgccgg aggcagcagg tgaagtggag cgtctgattg ccatcctttt gccgctgcgt    1740
ctggacgcga tcacgggccc agaggaggag ggtggccgtc tggaaaccat tctgggttgg    1800
ccgctggcgg agcgtaccgt cgtgattccg agcgccattc cgaccgaccc gcgtaatgtc    1860
ggcggcgact ggatccgtc cagcatcccg gacaaagaac aagctattag cgcgctgcct    1920
gattatgcga gcaaaaagaa acgtaagcgt cgtgaagacc tgaagtaa                 1968
```

<210> SEQ ID NO 3
<211> LENGTH: 2201
<212> TYPE: DNA
<213> ORGANISM: artificial sequence
<220> FEATURE:
<223> OTHER INFORMATION: sequence encoding fusion protein

<400> SEQUENCE: 3

```
gaattcgaaa ttaatacgac tcactatagg gagaccacaa cggtttccct ctagaaataa       60
ttttgtttaa ctttaagaag gagatatacc atgagcggtt ctcatcacca tcaccaccat     120
agcagcggta ttaaggtcg catgcacctg accccacact ggattccact ggtcgcgagc      180
ctgggcctgc tggcgggtgg cagctttgcg agcgctgcag aagaggcctt cgacctgtgg     240
aatgagtgtg cgaaagcatg tgttctggac ttgaaggatg gcgttcgcag cagccgcatg     300
```

```
agcgtcgatc cggcaattgc ggataccaac ggtcaaggtg ttctgcatta tagcatggtt    360
ctggaaggtg gcaatgacgc gctgaagttg gcgatcgaca atgcgctgag cattacctct    420
gatggcctga cgattcgcct ggagggtggt gttgagccga caaaccagt  ccgctacagc    480 tacacccgtc aagcgcgcgg tagctggagc ctgaactggc tggttccgat cggtcacgaa    540
aaacctagca acatcaaggt tttcattcat gagctgaacg ctggcaatca actgtcgcac    600
atgagcccga tttataccat tgaaatgggt gatgagctgc tggccaagct ggcacgtgat    660
gcaacgtttt tcgtccgtgc ccacgaatct aatgagatgc aacctacgct ggctatcagc    720
cacgcgggcg tgagcgttgt gatggcccaa gcgcaaccgc gtcgtgagaa gcgttggagc    780
gaatgggcca gcggcaaggt tctgtgtttg ctggatccgc tggacggtgt gtacaattat    840
ctggcgcagc agcgttgcaa cctggatgac acctgggaag gtaagattta tcgtgtgctg    900
gccggtaatc ctgcaaaaca tgacctggac attaaaccga ccgtcatctc ccaccgcctg    960
cacttcccgg agggcggtag cttggcagca ctgaccgcac accaggcgtg ccatctgccg   1020
ctggaaacct tcacccgtca ccgtcagccg cgtggttggg aacagctgga gcaatgcggt   1080
tatccagtgc aacgtctggt cgcactgtac ctggcgcgcg cctgtcctg  gaatcaggtc   1140 gaccaggtga tccgtaacgc attggcaagc ccgggcagcg gtggtgatct gggcgaggcc   1200
atccgtgagc aaccggagca agcacgtctg gcactgaccc tggccgccgc cgaaagcgaa   1260
cgcttcgttc gtcaaggtac tggtaatgac gaggcgggtg cggcctccgc ggatgtcgtg   1320
agcctgacgt gcccggttgc tgcgggtgag tgcgcgggtc cggctgacag cggcgatgct   1380
ctgctggagc gtaattatcc gaccggtgcc gaatttctgg gcgacggtgg cgatatcagc   1440
ttcagcacgc gcggtactca gaactggacc gttgaacgcc tgctgcaggc gcatcgtcag   1500
ctggaggaac gtggctatgt tttcgtcggt taccacggta ctttcctgga agctgcacaa   1560
agcattgttt ttggcggtgt ccgtgcacgc agccaggacc tggatgcgat ctggcgtggt   1620
ttctacatcg ccggtgaccc ggcgctggcg tacggctatg ctcaagatca agaaccggat   1680
gcgcgtggtc gtattcgcaa tggtgcattg ctgcgtgtgt atgtcccacg tagcagcttg   1740 ccgggttttct accgtacggg tttgacgctg cagcgccgg  aggcagcagg tgaagtggag   1800
cgtctgattg ccatcctttt gccgctgcgt ctggacgcga tcacgggccc agaggaggag   1860
ggtggccgtc tggaaaccat tctggttgg  ccgctggcgg agcgtaccgt cgtgattccg   1920
agcgccattc cgaccgaccc gcgtaatgtc ggcggcgact ggatccgtc  cagcatcccg   1980 gacaaagaac aagctattag cgcgctgcct gattatgcga gcaaaagaa  acgtaagcgt   2040 cgtgaagacc tgaagtaact aactaagatc cggtaagatc cggctgctaa caaagcccga   2100
aaggaagctg agttggctgc tgccaccgct gagcaataac tagcataacc ccttggggcc   2160
tctaaacggg tcttgagggg tttttttgctg gtaccaagct t                      2201
```

<210> SEQ ID NO 4
<211> LENGTH: 660
<212> TYPE: PRT
<213> ORGANISM: artificial sequence
<220> FEATURE:
<223> OTHER INFORMATION: fusion protein

<400> SEQUENCE: 4

Met Ser Gly Ser His His His His His His Ser Ser Gly Ile Glu Gly
1               5                   10                  15

Arg Met His Leu Thr Pro His Trp Ile Pro Leu Val Ala Ser Leu Gly

```
                    20                  25                  30
Leu Leu Ala Gly Gly Ser Phe Ala Ser Ala Glu Glu Ala Phe Asp
             35                  40                  45
Leu Trp Asn Glu Cys Ala Lys Ala Cys Val Leu Asp Leu Lys Asp Gly
 50                  55                  60
Val Arg Ser Ser Arg Met Ser Val Asp Pro Ala Ile Ala Asp Thr Asn
 65                  70                  75                  80
Gly Gln Gly Val Leu His Tyr Ser Met Val Leu Glu Gly Gly Asn Asp
             85                  90                  95
Ala Leu Lys Leu Ala Ile Asp Asn Ala Leu Ser Ile Thr Ser Asp Gly
            100                 105                 110
Leu Thr Ile Arg Leu Glu Gly Val Glu Pro Asn Lys Pro Val Arg
            115                 120                 125
Tyr Ser Tyr Thr Arg Gln Ala Arg Gly Ser Trp Ser Leu Asn Trp Leu
            130                 135                 140
Val Pro Ile Gly His Glu Lys Pro Ser Asn Ile Lys Val Phe Ile His
145                 150                 155                 160
Glu Leu Asn Ala Gly Asn Gln Leu Ser His Met Ser Pro Ile Tyr Thr
            165                 170                 175
Ile Glu Met Gly Asp Glu Leu Leu Ala Lys Leu Ala Arg Asp Ala Thr
            180                 185                 190
Phe Phe Val Arg Ala His Glu Ser Asn Glu Met Gln Pro Thr Leu Ala
            195                 200                 205
Ile Ser His Ala Gly Val Ser Val Val Met Ala Gln Ala Gln Pro Arg
            210                 215                 220
Arg Glu Lys Arg Trp Ser Glu Trp Ala Ser Gly Lys Val Leu Cys Leu
225                 230                 235                 240
Leu Asp Pro Leu Asp Gly Val Tyr Asn Tyr Leu Ala Gln Gln Arg Cys
            245                 250                 255
Asn Leu Asp Asp Thr Trp Glu Gly Lys Ile Tyr Arg Val Leu Ala Gly
            260                 265                 270
Asn Pro Ala Lys His Asp Leu Asp Ile Lys Pro Thr Val Ile Ser His
            275                 280                 285
Arg Leu His Phe Pro Glu Gly Gly Ser Leu Ala Ala Leu Thr Ala His
            290                 295                 300
Gln Ala Cys His Leu Pro Leu Glu Thr Phe Thr Arg His Arg Gln Pro
305                 310                 315                 320
Arg Gly Trp Glu Gln Leu Glu Gln Cys Gly Tyr Pro Val Gln Arg Leu
            325                 330                 335
Val Ala Leu Tyr Leu Ala Ala Arg Leu Ser Trp Asn Gln Val Asp Gln
            340                 345                 350
Val Ile Arg Asn Ala Leu Ala Ser Pro Gly Ser Gly Asp Leu Gly
            355                 360                 365
Glu Ala Ile Arg Glu Gln Pro Glu Gln Ala Arg Leu Ala Leu Thr Leu
            370                 375                 380
Ala Ala Ala Glu Ser Glu Arg Phe Val Arg Gln Gly Thr Gly Asn Asp
385                 390                 395                 400
Glu Ala Gly Ala Ala Ser Ala Asp Val Val Ser Leu Thr Cys Pro Val
            405                 410                 415
Ala Ala Gly Glu Cys Ala Gly Pro Ala Asp Ser Gly Asp Ala Leu Leu
            420                 425                 430
Glu Arg Asn Tyr Pro Thr Gly Ala Glu Phe Leu Gly Asp Gly Gly Asp
            435                 440                 445
```

-continued

```
Ile Ser Phe Ser Thr Arg Gly Thr Gln Asn Trp Thr Val Glu Arg Leu
    450             455             460
Leu Gln Ala His Arg Gln Leu Glu Glu Arg Gly Tyr Val Phe Val Gly
465             470             475             480
Tyr His Gly Thr Phe Leu Glu Ala Ala Gln Ser Ile Val Phe Gly Gly
            485             490             495
Val Arg Ala Arg Ser Gln Asp Leu Asp Ala Ile Trp Arg Gly Phe Tyr
            500             505             510
Ile Ala Gly Asp Pro Ala Leu Ala Tyr Gly Tyr Ala Gln Asp Gln Glu
            515             520             525
Pro Asp Ala Arg Gly Arg Ile Arg Asn Gly Ala Leu Leu Arg Val Tyr
    530             535             540
Val Pro Arg Ser Ser Leu Pro Gly Phe Tyr Arg Thr Gly Leu Thr Leu
545             550             555             560
Ala Ala Pro Glu Ala Ala Gly Glu Val Glu Arg Leu Ile Gly His Pro
            565             570             575
Leu Pro Leu Arg Leu Asp Ala Ile Thr Gly Pro Glu Glu Glu Gly Gly
            580             585             590
Arg Leu Glu Thr Ile Leu Gly Trp Pro Leu Ala Glu Arg Thr Val Val
    595             600             605
Ile Pro Ser Ala Ile Pro Thr Asp Pro Arg Asn Val Gly Gly Asp Leu
    610             615             620
Asp Pro Ser Ser Ile Pro Asp Lys Glu Gln Ala Ile Ser Ala Leu Pro
625             630             635             640
Asp Tyr Ala Ser Gln Pro Gly Lys Pro Lys Lys Arg Lys Arg Arg
            645             650             655
Glu Asp Leu Lys
            660
```